United States Patent [19]
Tordoff

[11] 4,320,651
[45] Mar. 23, 1982

[54] HOT DEFORMATION TESTING METHOD AND APPARATUS

[75] Inventor: William L. Tordoff, Worthington, Ohio

[73] Assignee: Ashland Oil, Inc., Ashland, Ky.

[21] Appl. No.: 132,262

[22] Filed: Mar. 20, 1980

[51] Int. Cl.³ .......................... G01N 3/18; G01N 3/20
[52] U.S. Cl. ......................................... 73/15.6; 73/852
[58] Field of Search ................. 73/15.6, 849, 851, 852

[56] References Cited
U.S. PATENT DOCUMENTS

| | | | |
|---|---|---|---|
| 2,479,984 | 8/1949 | Stock | 73/15.6 |
| 2,495,746 | 1/1950 | Lubin | 73/15.6 |
| 2,504,985 | 4/1950 | Kallas et al. | 73/15.6 |
| 3,774,440 | 11/1973 | Martinelli | 73/15.6 |

FOREIGN PATENT DOCUMENTS 1159952 7/1969 United Kingdom ................. 73/15.6

*Primary Examiner*—Charles A. Ruehl
*Attorney, Agent, or Firm*—Wood, Herron & Evans

[57] ABSTRACT

A hot deformation tester to determine the ability for a sand and binder combination to withstand high ambient temperature without deforming excessively. An insulated chamber receives an elongated core sample on two spaced supports, and applies a weight to the center of the sample. The sample is subjected to ambient temperature of about 600° F. A deflection probe in engagement with the bottom of the sample measures the deformation of the sample.

4 Claims, 3 Drawing Figures

HOT DEFORMATION TESTING METHOD AND APPARATUS

This invention relates to apparatus for testing their resistance to deformation of a sand core when it is subjected to heat.

The invention has specific application to foundry practices wherein molten metal is poured into a mold and permitted to solidify there in order to form a casting. In such foundry practice, it is conventional to use cores formed from sand and a binder to define cavities or other configurations in the casting. The cores are placed in the mold and the molten metal flows around the cores, the cores forming the desired cavities in precise locations within the castings. In the casting of a cylinder block for an internal combustion engine, for example, cores are used to form the cylinders while the external surface of the block is formed by the mold.

There are presently available a wide variety of binder systems which are used to form cores. The binder system selected by a foundry might depend on a number of circumstances such as the machinery by which the cores are formed, the ambient conditions of the foundry, the type of metal that is used to form the casting and the like. On the one hand, the binders must be strong enough to form the core and permit it to be handled until it is finally subjected to the molten metal by which the casting is made. On the other hand, the binder must be capable of being sufficiently weakened by being subjected to the molten metal that it will permit the core to disintegrate once the cast metal has solidified in order that the sand can be shaken out of the casting after the casting process has been completed.

A process wherein the part is cast in a semi-permanent mold creates special problems. A semi-permanent mold is a mold formed from metal, as contrasted to sand. The metal mold forms the outside surface of the casting. The internal cavities, however, must be formed from sand cores, as described above.

The metallic mold is normally maintained at a relatively high temperature, that is, at least about 600° F., so that the metallic mold does not chill the cast metal too rapidly when it is poured. The cast metal must be permitted to flow into all of the areas of the mold, for otherwise an imperfect casting will be formed, and therefore must remain quite fluid during the first few seconds of the pour.

Prior to the casting operation, the core must be positioned in the hot metal mold, and it must remain there for at least a short time until the mold is closed and the molten metal is poured into it to form the casting.

Subjecting the core to the high temperature of the mold may cause the binder to become soft and cause the core within the mold to distort before the molten metal hits it. If the core distorts or sags while it is in the mold, the cavity in the casting which the core is to form will be misaligned and the casting will be imperfect.

A device known as a hot deformation indicator is currently on the market. The device is also known as a dilatometer. It does not provide any measurement of the resistance of a core to deformation when it is subjected to heat of about 600° F., namely, the heat of the metallic mold before pouring. Rather, the hot distortion tester determines the probability of the core to resist the molten metal when the molten metal strikes the core.

It has been an objective of the present invention to provide a method and apparatus which can be used to test the resistance to deformation of a sand core, and particularly its binder, which is subjected to an ambient temperature approximating that of a semipermanent mold of the type described above.

To this end, the invention provides for a housing, a pair of spaced supports for a test core, a weight to be placed upon the test core, and means for subjecting the test core to radiant heat. Means are also provided to test the extent that the test core distorts or deflects under the force of the weight which rests upon it during the testing procedure.

Using a standard test sample having the dimensions $1 \times 1 \times 8$ inches (for example), and placing such a sample on the supports, while subjecting the core to heat, it is possible to run tests of many binder systems in order to determine the best combinations of sands and binders for making cores for semipermanent molds which must resist hot deformation.

The invention will become more readily apparent from the following detailed description taken in conjunction with the accompanying drawings in which.

Figure 1:
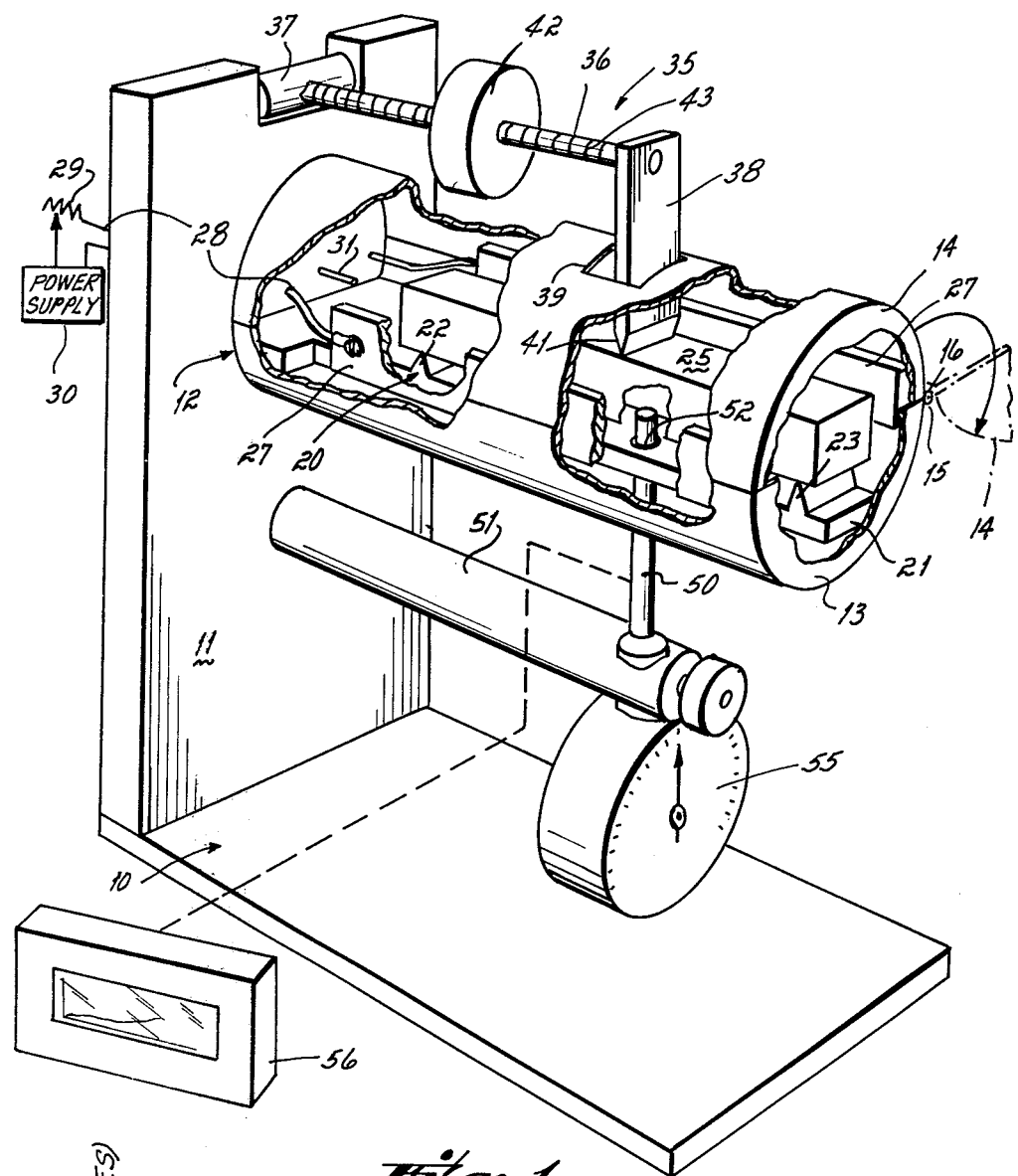
FIG. 1 is a perspective view of the apparatus of the present invention.

The testing apparatus is mounted on a base 10 which has a vertical support wall 11 fixed to one end. An insulated chamber 12 is mounted on the upper portion of the wall 11. The chamber is formed by a lower housing section 13 and an upper cover 14. The lower housing section has a horizontal edge, the upper cover being connected to the lower housing section by hinges 16 secured to the edge 15 of the lower housing section. The cover 14 is pivotable from a closed position as illustrated in solid lines to an open position illustrated by the fragmentary phantom lines.

Within the chamber and supported by the lower section is a core sample support 20 consisting of an elongated horizontal plate 21 having two spaced, upwardly-projecting knife edges 22 and 23. In the illustrated form of the invention, the knife edges are spaced apart by 7 inches. The knife edges are adapted to receive and provide support for the ends of a core sample 25 which is, for example $1 \times 1 \times 8$ inches in dimensions.

Positioned alongside the core sample support 20 are two elongated, 400 watt radiant heaters 27 which are adapted to raise the ambient temperature surrounding the core sample to at least about 650° F. The heaters are connected through cables 28 and a rheostat 29 to a power supply 30. The rheostat is provided in order to permit variations in temperature for differing types of testing procedures which may be required. A temperature probe or thermocouple 31 extends into the chamber to permit the operator to maintain the temperature at a predetermined level.

A force applicator 35 overlies the core sample support 20 and is adapted to apply a weight to the core sample 25. The applicator includes an elongated, generally horizontal, rod 36 which is pivoted at 37 to the vertical support wall 11. A depending vertical element 38 is connected to the end of the rod 36 and projects through a hole 39 in the cover 14 so as to be engageable with the core sample 25. The lower edge 41 of the element 38 can be a knife edge or could be provided with a slight radius. A weight 42 is mounted on the rod 36 for movement therealong. A ruled scale 43 is provided on the upper surface of the rod and is preferably calibrated in the weight applied at the edge 41 of the vertical element for each horizontal position of the weight 42.

A deflection probe 50 is mounted on a horizontal arm 51 fixed to the vertical wall 11. The probe projects upwardly through the chamber 12 and through a hole 52 in the plate 21. The upper end of the probe is engageable with the lower surface of the core sample 25. The lower end of the probe is connected to a dial indicator 55 which indicates the amount of deflection of the core when it is subjected to heat and the overlying weight. The probe is also connected, as indicated diagrammatically, to a strip chart 56 which provides a recorded visual display of the amount of deflection versus the period of time during which the core sample is subjected to the heat and weight.

The invention is to be used primarily in determining what combinations of sand and binder will have sufficient resistance to deformation when subjected to an ambient temperature of at least about 600° F. Provision is made in the apparatus for varying the temperature as well as varying the weight applied to the core sample so as to simulate differing conditions that might be encountered in different casting operations. It, of course, will be understood that in comparing one sand and binder system to another, all conditions should be maintained as close to identical as possible except for the variable, e.g., the binder, which is being used.

The operation first requires the preparation of the sand mix to be tested in accordance with the standard practice. Samples which are $1 \times 1 \times 8$ inches are formed in the core-making equipment normally used for the particular sand and binder combination. Preferably, at least three dog bones should be made along with the main core sample. The term "dog bone" is that used in the art to describe the sample which is prepared in known equipment for testing the tensile strength of sand and binder combinations. In the present testing procedure, the dog bones are not used to produce any information concerning the ability of the cores to resist hot deformation, but rather are used to take standard tensile tests of the binder and sand combination. These tensile test results provide assurance of control data, that is, that there are no aberrations in the expected quality of the cores produced from that sand and binder combination. If it is desired to measure the actual temperature of the core sample, a $3/16 \times 2$ inch hole may be drilled in the end of the sample 25 and a thermocouple inserted into it. This is an optional, alternative approach. It is believed satisfactory to measure the ambient temperature surrounding the core sample.

Figure 2A:
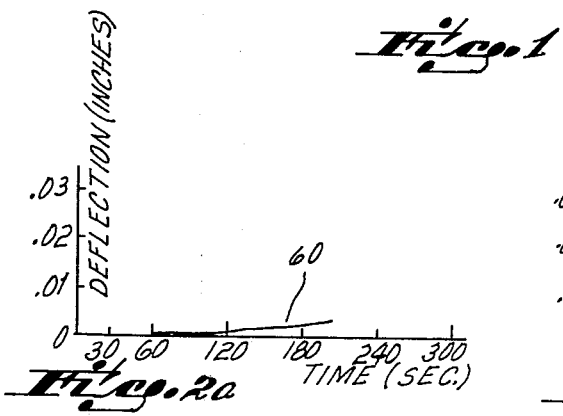
FIGS. 2a and 2b are diagrammatic views of curves illustrating the method of testing sand and binder combinations.
Figure 2B:
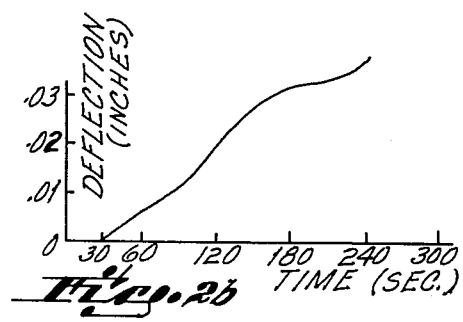

With the heaters 27 energized and the temperature at approximately 600° F., the chamber is opened, the core sample is placed on the knife edges 22 and 23, the cover 14 is closed, and a load of about 1600 grams is applied through the force applicator 35 to the core sample. The strip chart 56 is operated for about five minutes or until the core sample breaks. The curves produced by the strip chart may appear as shown in FIGS. 2a and 2b. FIG. 2a shows a test run for three minutes. The slope of the curve indicated at 60 is very gradual and shows a deformation of less than 0.005 inch in 180 seconds. This would indicate that that sand and binder combination will produce a satisfactory core from the standpoint of its ability to resist deformation. Another curve was prepared by the strip chart 56 and is shown in FIG. 2b. There, a different binder was used with the same sand. It can be seen that the sample broke in about four minutes, and in about three minutes the sample had deformed in excess of 0.030 inch. That result would indicate that the binder used to prepare the core of FIG. 2b is unacceptable from the standpoint of its ability to resist hot deformation. It should be understood that that binder might be satisfactory in a higher ratio of binder to sand, or it might be satisfactory with a different sand. Further tests on the instant apparatus would be required to make those determinations. It should also be understood that the binder might be satisfactory for other types of casting operations where resistance to hot deformation is not required.

I claim:

1. A hot deformation tester comprising,
a chamber,
a pair of horizontally-spaced supports in said chamber for receiving and supporting an elongated core sample,
a force applicator centered above said supports and adapted to apply a force to the upper surface of a core sample mounted on said supports,
a deflection probe located between said supports and engageable with the underside of said core sample,
means connected to said probe for displaying the magnitude of movement of said probe,
heaters disposed in said chamber for raising the temperature surrounding said core sample to at least about 600° F.,
said chamber comprising a lower elongated housing section which is open at its top and which has a longitudinal edge at one side thereof, and
an upper cover, said cover being hinged to the longitudinal edge of said lower housing section, and being swingable between a closed position and an open position wherein said supports and core sample are exposed.

2. Apparatus as in claim 1,
said chamber being mounted on a vertical support,
said cover having a hole in the central portion thereof,
said force applicator comprising an elongated rod pivoted at one end to said vertical support and horizontally overlying said cover when it is in closed position,
a vertical element fixed to the end of said rod and projecting through said hole for engagement with said core sample.

3. Apparatus as in claim 2 further comprising a weight mounted on said rod for movement therealong to vary the weight applied to said core sample.

4. The method of determining the suitability of a sand and binder combination for cores which are to be used in metallic molds comprising the steps of,
mixing the binder with sand,
forming an elongated core from said sand and binder mixture,
supporting said core at its ends while placing a weight at its center portion,
subjecting said core to a temperature of at least about 600° F., and
measuring the deflection of the center portion of said core.

* * * * *